June 5, 1973 W. H. JESSEL. JR., ET AL Plant Pat. 3,354
CHRYSANTHEMUM PLANT
Filed May 17, 1971
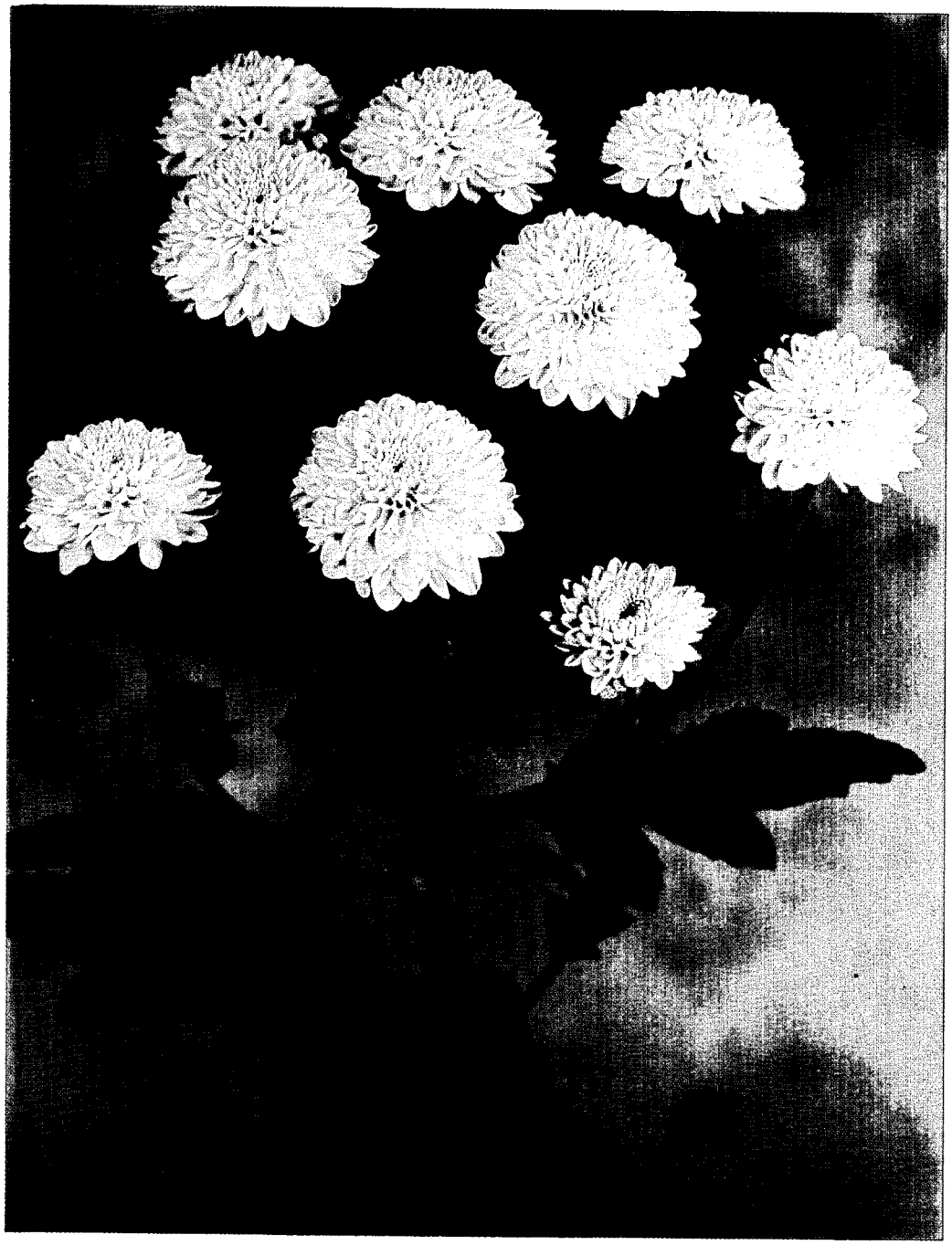
INVENTORS
WALTER H. JESSEL, JR.,
WILLIAM E. DUFFETT
BY
Oberlin, Maky, Donnelly & Renner
ATTORNEYS

United States Patent Office

Plant Pat. 3,354
Patented June 5, 1973

3,354

CHRYSANTHEMUM PLANT

Walter H. Jessel, Jr., Doylestown, and William E. Duffet, Akron, Ohio, assignors to Yoder Brothers, Inc., Barberton, Ohio

Filed May 17, 1971, Ser. No. 144,191
Int. Cl. A01h *5/00*
U.S. Cl. Plt.—80 1 Claim

The present invention comprises a new and distinct variety of chrysanthemum plant which is a seedling of parents identified as #611868-5×#63340-1. Both parents are unpatented and identified for breeding purposes by the above numbers to distinguish the same from other parents in the same breeding program.

The new cultivar is similar in many respects to the well-known, unpatented cultivar Carillon, having the same characteristics as Carillon of:

(1) Flower form which is a formal pompon.
(2) Stem strength—strong and wiry.
(3) Lack of pollen.
(4) Identical keeping qualities—7–10 days.
(5) Tolerance to varying temperature and light conditions.

The new variety is distinguished from Carillon by the following characteristics:

(1) ½″ larger flowers.
(2) A minimum of 4 more flowers per stem, thereby providing greater productivity.
(3) 3″–4″ additional vigor when grown under identical conditions.
(4) Stipules present and clearly evident at base of petiole. There are no stipules on Carillon.
(5) A smoother lavender color with less fading under high temperature, high light conditions, thereby providing a more uniform color over the petal and a more attractive appearance.
(6) A broader, less sharply pointed petal.
(7) A larger, darker colored leaf with less indentation, serration, and prominence of ribs and veins.

The new cultivar was selected from the progeny of the designated cross and when asexually reproduced by cuttings at Barberton, Ohio, has been found to retain its distinctive characteristics through successive propagations.

The new cultivar when grown in the vicinity of Barberton, Ohio, has a response period of approximately 10 weeks, and the following detailed description is based on observations made of the new cultivar in a greenhouse in Barberton, Ohio. The response time, color, vigor, and blooming period may vary significantly with varying environmental conditions such as temperature, day length, and light intensity. Suggested flowering in the northern United States is from mid-March to mid-November; in coastal California, year-round, and in the southern states, December through April.

The accompanying drawing shows the unique characteristics of the new cultivar, the color being as nearly true as possible with color illustrations of this type.

In the description which follows, color references are made to the Munsell Color Book, 1963 edition, and comparisons are made with the cultivar Carillon. Where only a single value or description appears for the new cultivar, the same value or description applies also to the comparison cultivar.

Botanical classification: *Chrysanthemum morifolium*

| | Spartan | Carillon |
|---|---|---|
| Bloom: | | |
| Size | 2⅜″ | 1¾″. |
| Fully expanded | 3″ | 2½″. |
| Borne | On elongated pedicels in clusters of 9–10 | On elongated pedicels in clusters of 5–6. |
| Stems | Strong and wiry | |
| Form | Formal pompon | |
| Permanence | 7–10 days | |
| Color: | | |
| Center of flower | Lavender, 10P7/4 to lavender, 10P7/6 | Greenish yellow, 10Y8.5/6. |
| Base of petals | Lavender, 10P7/4 to lavender, 10P8/4 | Lavender 7P7/2 to pale lavender, 10P9/1. |
| Inside of petals | do | Lavender, 10P8/6 to light lavender, 10P8/4. |
| Reverse of petals | Light lavender, 10P9/2, to light lavender, 10RP 9/1. | Lavender, 7P7/2 to pale lavender, 10P9/1. |
| Tonality from a distance | Lavender | Lavender. |
| Discoloration | Light lavender | Grey-lavender. |
| Petals: | | |
| Texture | Smooth | |
| Appearance and form | Open at base, moderately keeled, tapering to a rounded point. | Open at base, deeply keeled tapering to a point |
| Arrangement | Composite, whorled on a single receptacle | |
| Persistence | Resist shatter | |
| Fragrance | Typical chrysanthemum | |
| Reproductive organs: | | |
| Stamen, anthers | None | |
| Pollen | do | |
| Arrangement | do | |
| Styles | Present | |
| Length | Short | |
| Ovaries | At base of petal attached to receptacle | |
| Plant: | | |
| Form | Herbaceous | |
| Growth | Upright | |
| Height, depending on culture | 44″–48″ | 40″–44″. |
| Spread | None when grown single stem to slight when grown pinched. | |
| Foliage: | | |
| Top side | Dark green 10GY3/2 | Green, 10GY3/4. |
| Size | 7½″ long, 4½″ wide | 6¼″ long, 2⅞″ wide. |
| Quantity | Numerous | |
| Shape | Palmate | |
| Texture | Smooth | |
| Ribs and veins | Prominent | Very prominent. |
| Edge | Moderately indented | Deeply indented. |
| Serration | Slight | Moderate. |
| Underside | Light green, 7.5GY6/4 | Light green, 10GY5/4. |
| Stipules | Prominent at base of petiole | No stipules. |

We claim:

1. A new and distinct variety of chrysanthemum characterized particularly as to its uniqueness when compared to the cultivar Carillon by its ½″ larger flowers; greater flower production, averaging 4 more flowers per stem; 3″–4″ more vigor; stipules formation; a smoother lavender color with less fading under high temperature, high light conditions; a broader, less sharply pointed petal; and by its larger, darker, less indented, and serrated foliage with less prominent ribs and veins.

No references cited.

ROBERT E. BAGWILL, Primary Examiner